United States Patent
Lau et al.

(10) Patent No.: US 11,250,938 B2
(45) Date of Patent: Feb. 15, 2022

(54) METHOD, APPARATUS, AND COMPUTER PROGRAM PRODUCT FOR SUBMISSION OF MEDICAL ELIGIBILITY AND CLAIM DATA

(71) Applicant: McKesson Corporation, Irving, TX (US)

(72) Inventors: Jamie Lau, Atlanta, GA (US); Elizabeth Kaye, Suwanee, GA (US); Roy Toney, Woodstock, GA (US); Ramond McBeth, Decatur, GA (US); Anika Khare, Alpharetta, GA (US); James Adair, Alpharetta, GA (US)

(73) Assignee: MCKESSON CORPORATION, Irving, TX (US)

( * ) Notice: Subject to any disclaimer, the term of this patent is extended or adjusted under 35 U.S.C. 154(b) by 28 days.

(21) Appl. No.: 16/826,417

(22) Filed: Mar. 23, 2020

(65) Prior Publication Data

US 2021/0295970 A1    Sep. 23, 2021

(51) Int. Cl.
| | |
|---|---|
| *G06Q 30/00* | (2012.01) |
| *G16H 20/10* | (2018.01) |
| *G06Q 10/10* | (2012.01) |
| *G06Q 30/02* | (2012.01) |

(52) U.S. Cl.
CPC ............. *G16H 20/10* (2018.01); *G06Q 10/10* (2013.01); *G06Q 30/0224* (2013.01); *G06Q 30/0239* (2013.01)

(58) Field of Classification Search
CPC .... G16H 20/10; G06Q 10/10; G06Q 30/0224; G06Q 30/0239
USPC .......................................................... 705/2
See application file for complete search history.

(56) References Cited

U.S. PATENT DOCUMENTS

| | | |
|---|---|---|
| 10,924,585 B1 | 2/2021 | Harris et al. |
| 10,929,932 B1 | 2/2021 | Golden et al. |
| 10,999,224 B1 | 5/2021 | Frechen et al. |
| 2004/0006490 A1* | 1/2004 | Gingrich ................ G16H 40/67 705/2 |

(Continued)

OTHER PUBLICATIONS

G. M. McGrath and E. More, "Data integration along the healthcare supply chain: the pharmaceutical extranet gateway project," 2001, Proceedings of the 34th Annual Hawaii International Conference on System Sciences, 2001, pp. 8 pp.-, doi: 10.1109/HICSS.2001. 926556.*

*Primary Examiner* — Sun M Li
(74) *Attorney, Agent, or Firm* — Alston & Bird LLP (57) ABSTRACT

A method, apparatus and computer program product are provided to facilitate the efficient generation and submission of medical eligibility and medical claim data. In a method, a modified pharmacy benefits transaction associated with a patient is received that is formatted in a first predefined format. The modified pharmacy benefits transaction is parsed to determine an indicator and data is extracted from the modified pharmacy benefits transaction based on the indicator. A database is accessed to retrieve additional data that is at least partly based on a pharmacy with which the source is associated, a potential payor of the medical transaction or a medication that is a subject of the medical transaction. A medical transaction is generated that includes the extracted data and the additional data and formatted in a second predefined format. A response to the medical transaction is then transmitted to a source for display to a user.

12 Claims, 5 Drawing Sheets

(56) References Cited

U.S. PATENT DOCUMENTS

| | | | | |
|---|---|---|---|---|
| 2005/0154627 | A1* | 7/2005 | Zuzek | G16H 20/10 |
| | | | | 705/2 |
| 2009/0030727 | A1* | 1/2009 | Revak | G06Q 10/00 |
| | | | | 705/3 |
| 2009/0327363 | A1* | 12/2009 | Cullen | G16H 20/10 |
| 2010/0285821 | A1* | 11/2010 | Smeeding | G06Q 30/0225 |
| | | | | 455/466 |
| 2011/0029321 | A1* | 2/2011 | Rourke | G06F 16/986 |
| | | | | 705/2 |
| 2013/0218595 | A1* | 8/2013 | Burkett | G06Q 40/00 |
| | | | | 705/3 |
| 2015/0149197 | A1* | 5/2015 | Guinan | G06Q 40/08 |
| | | | | 705/2 |

\* cited by examiner

METHOD, APPARATUS, AND COMPUTER PROGRAM PRODUCT FOR SUBMISSION OF MEDICAL ELIGIBILITY AND CLAIM DATA

TECHNOLOGICAL FIELD

Embodiments of the present invention relate generally to healthcare transactions and, more particularly, to methods, apparatuses, and computer program products for submission of medical eligibility and medical claim data.

BACKGROUND

In the healthcare services industry, a pharmacy may assist a patient in many ways, including billing to a pharmacy benefit plan associated with the patient for a particular treatment, such as a prescription medication, immunization, or the like. However, some treatments may not be billable toward a pharmacy benefit plan and may only be billable to a medical benefit plan. Conventional pharmacy workflows lack an effective means to process and submit medical transactions, such as transactions to determine a patient's eligibility for medical benefits, a medical claim, and/or the like. For example, one barrier contributing to this deficiency is that pharmacy transactions typically utilize the National Council for Prescription Drug Program (NCPDP) communications standard, whereas medical benefit transactions may require utilization of a different standard (e.g., X12 or another format). This disconnect increases the challenges for pharmacies in relation to extending their services in an efficient manner.

BRIEF SUMMARY

A method, apparatus, and computer program product are provided in accordance with an example embodiment in order to facilitate the efficient generation and submission of medical eligibility and medical claim data. As a result, submitters, such as pharmacies are alleviated from utilizing conventional, time-consuming alternatives. By providing a means for generation, submission, and processing of medical transactions, the method, apparatus, and computer program product of an example embodiment improve the efficiency and effectiveness of pharmacy workflows. Similarly, the method, apparatus and computer program product of an example embodiment alleviate uncertainty and potentially reduce the load on a network when submitting medical transactions by providing timely responses, thereby providing a technical advantage to the network and the devices communicating via the network by reducing network traffic and avoiding the consumption of the processing resources otherwise required to construct, transmit, receive, and process the additional messages intended to follow up on a medical transaction that are now no longer needed.

In one embodiment, a computer-implemented method is provided with the computer-implemented method comprising receiving a modified pharmacy benefits transaction associated with a patient and formatted in accordance with a first predefined format from a source. The computer-implemented method further comprises parsing the modified pharmacy benefits transaction to determine that the modified pharmacy benefits transaction comprises an indicator. The computer-implemented method further comprises extracting data from one or more fields of the modified pharmacy benefits transaction based on the indicator. The computer-implemented method further comprises accessing a database and retrieving additional data from the database. The additional data to be retrieved is based at least in part on one or more of a pharmacy with which the source is associated, a potential payor of the medical transaction or a medication that is a subject of the medical transaction. The computer-implemented method further comprises generating a medical transaction comprising the extracted data and the additional data, wherein the medical transaction is formatted in accordance with a second predefined format. The computer-implemented method further comprises receiving a response to the medical transaction. The computer-implemented method further comprises causing transmission of the response to the source for display to a user.

In some embodiments of the computer-implemented method, the indicator comprises a medical eligibility check indicator, and the medical transaction comprises a medical eligibility check request. In some embodiments of the computer-implemented method, the response comprises a transaction identifier in an instance in which a timeout for the medical eligibility check request has occurred, and in other embodiments of the computer-implemented method, the response comprises an indication of patient eligibility in an instance in which the timeout for the medical eligibility check request has not occurred. In some embodiments, the computer-implemented method further comprises monitoring for receipt of a response associated with the medical eligibility check request. In some embodiments, the computer-implemented method further comprises, in an instance in which it is determined that the response to the medical eligibility check request has not been received for a time exceeding the timeout value, generating a transaction identifier for the medical eligibility check request and causing transmission of the transaction identifier to the source for display to a user. In some embodiments of the computer-implemented method, the indicator comprises a medical benefit claim indicator, wherein the medical transaction comprises a medical benefit claim, and wherein the response comprises an indication of acceptance of the medical benefit claim by the request processor. In some embodiments, the computer-implemented method further comprises formatting the response to be in accordance with a third predefined format associated with a pharmacy. In some embodiments the computer-implemented method further comprises, in an instance in which the extracted data and the additional data are determined to not include data required for generation of a medical transaction: generating a rejection message comprising an indication of rejection of the modified pharmacy benefits transaction and causing transmission of the rejection message to the source.

In another aspect, an apparatus is provided comprising at least one processor and at least one memory including computer program code with the at least one memory and the computer program code configured to, with the processor, cause the apparatus to at least receive a modified pharmacy benefits transaction associated with a patient and formatted in accordance with a first predefined format from a source. The at least one memory and the computer program code are further configured to, with the processor, cause the apparatus to parse the modified pharmacy benefits transaction to determine that the modified pharmacy benefits transaction comprises an indicator. The at least one memory and the computer program code are further configured to, with the processor, cause the apparatus to extract data from one or more fields of the modified pharmacy benefits transaction based on the indicator. The at least one memory and the computer program code are further configured to, with the processor, cause the apparatus to access a database and retrieve additional data from the database. The additional data to be retrieved is based at least in part on one or more of a pharmacy with which the source is associated, a potential payor of the medical transaction or a medication that is a subject of the medical transaction. The at least one memory and the computer program code are further configured to, with the processor, cause the apparatus to generate a medical transaction comprising the extracted data and the additional data, with the medical transaction being formatted in accordance with a second predefined format. The at least one memory and the computer program code are further configured to, with the processor, cause the apparatus to receive a response to the medical transaction. The at least one memory and the computer program code are further configured to, with the processor, cause the apparatus to cause transmission of the response to the source for display to a user.

In some embodiments of the apparatus, the indicator comprises a medical eligibility check indicator, and the medical transaction comprises a medical eligibility check request. In some embodiments of the apparatus, the response comprises a transaction identifier in an instance in which a timeout for the medical eligibility check request has occurred, and in other embodiments of the apparatus, the response comprises an indication of patient eligibility in an instance in which the timeout for the medical eligibility check request has not occurred. In some embodiments, the at least one memory and the computer program code are further configured to, with the processor, cause the apparatus to monitor for receipt of a response associated with the medical eligibility check request. In some embodiments, the at least one memory and the computer program code are further configured to, with the processor, cause the apparatus to, in an instance in which it is determined that the response to the medical eligibility check request has not been received for a time exceeding the timeout value, generate a transaction identifier for the medical eligibility check request and cause transmission of the transaction identifier to the source for display to a user. In some embodiments of the apparatus, the indicator comprises a medical benefit claim indicator, the medical transaction comprises a medical benefit claim, and the response comprises an indication of acceptance of the medical benefit claim by the request processor. In some embodiments, the at least one memory and the computer program code are further configured to, with the processor, cause the apparatus to format the response to be in accordance with a third predefined format associated with a pharmacy. In some embodiments, the at least one memory and the computer program code are further configured to, with the processor, cause the apparatus to, in an instance in which the extracted data and the additional data are determined to not include data required for generation of a medical transaction, generate a rejection message comprising an indication of rejection of the modified pharmacy benefits transaction and cause transmission of the rejection message to the source.

In another aspect, a computer program product is provided comprising at least one non-transitory computer-readable storage medium having computer-executable program code instructions stored therein with the computer-executable program code instructions comprising program code instructions to receive a modified pharmacy benefits transaction associated with a patient and formatted in accordance with a first predefined format from a source. The computer-executable program code instructions further comprise program code instructions to parse the modified pharmacy benefits transaction to determine that the modified pharmacy benefits transaction comprises an indicator. The computer-executable program code instructions further comprise program code instructions to extract data from one or more fields of the modified pharmacy benefits transaction based on the indicator. The computer-executable program code instructions further comprise program code instructions to access a database and retrieve additional data from the database. The additional data to be retrieved is based at least in part on one or more of a pharmacy with which the source is associated, a potential payor of the medical transaction or a medication that is a subject of the medical transaction. The computer-executable program code instructions further comprise program code instructions to generate a medical transaction comprising the extracted data and the additional data with the medical transaction being formatted in accordance with a second predefined format. The computer-executable program code instructions further comprise program code instructions to receive a response to the medical transaction. The computer-executable program code instructions further comprise program code instructions to cause transmission of the response to the source for display to a user.

In some embodiments of the computer program product, the indicator comprises a medical eligibility check indicator, and the medical transaction comprises a medical eligibility check request. In some embodiments of the computer program product, the response comprises a transaction identifier in an instance in which a timeout for the medical eligibility check request has occurred, and in other embodiments of the computer program product, the response comprises an indication of patient eligibility in an instance in which the timeout for the medical eligibility check request has not occurred. In some embodiments, the computer-executable program code instructions further comprise program code instructions to monitor for receipt of a response associated with the medical eligibility check request. In some embodiments, the computer-executable program code instructions further comprise program code instructions to, in an instance in which it is determined that the response to the medical eligibility check request has not been received for a time exceeding the timeout value, generate a transaction identifier for the medical eligibility check request and cause transmission of the transaction identifier to the source for display to a user. In some embodiments of the computer program product, the indicator comprises a medical benefit claim indicator, the medical transaction comprises a medical benefit claim, and the response comprises an indication of acceptance of the medical benefit claim by the request processor. In some embodiments, the computer-executable program code instructions further comprise program code instructions to format the response to be in accordance with a third predefined format associated with a pharmacy. In some embodiments, the computer-executable program code instructions further comprise program code instructions to, in an instance in which the extracted data and the additional data are determined to not include data required for generation of a medical transaction, generate a rejection message comprising an indication of rejection of the modified pharmacy benefits transaction and cause transmission of the rejection message to the source.

BRIEF DESCRIPTION OF THE DRAWINGS

Having thus described certain embodiments of the invention in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing device, it will be appreciated that the data may be sent directly to the other computing device or may be sent to the other computing device via one or more interlinking computing devices, such as, for example, one or more servers, relays, routers, network access points, and/or the like.

Additionally, as used herein, the terms 'circuitry' and/or 'module' refer to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a processor, e.g., a microprocessor(s) or a portion of a microprocessor(s), that require software or firmware for operation even if the software or firmware is not physically present. This definition of 'circuitry' and/or 'module' applies to all uses of these terms herein, including in any claims. As a further example, as used herein, the terms 'circuitry' and/or 'module' also include an implementation comprising one or more processors and/or portion(s) thereof and accompanying software and/or firmware. As another example, the terms 'circuitry' and/or 'module' as used herein also includes, for example, an applications processor integrated circuit, field programmable gate array, and/or other computing device.

OVERVIEW

As described above, pharmacies are typically equipped to handle operations related to prescription or pharmacy transactions and lack an effective means to process and submit medical transactions, such as transactions to determine a patient's eligibility for medical benefits, a medical claim, and/or the like. For example, pharmacies may be accustomed to billing to pharmacy benefits plans and may have methods in place in order to handle such a task, yet some medications, immunizations, and/or other treatments may be billable only to a medical benefits plan rather than a pharmacy benefits plan.

In certain situations, it may be desirable for a pharmacy to check for a patient's eligibility for coverage of a particular treatment under a medical benefits plan and/or bill to a medical benefits plan (e.g., submit a medical claim). In some embodiments, the pharmacy may initially submit a medical eligibility request or a medical benefits claim pursuant to the medical benefits plan. In other embodiments, the pharmacy may first submit an eligibility request or a claim pursuant to a pharmacy benefits and only submit a medical eligibility request or a medical benefits claim after a pharmacy benefits plan has issued a rejection and/or indication of no coverage for the particular medication, treatment, etc. However, conventional pharmacy workflows fail to provide an effective means for these options. For example, in the case of a medical eligibility check, a pharmacy may be forced to place phone calls to payers or utilize individual payer portals or medical benefits clearinghouse portals in order to determine eligibility. In the case of a medical claim, a pharmacy may have to fill out and utilize Health Care Financing Administration (HCFA) 1500 forms and/or individual payer portals or medical benefits clearinghouse portals. Additionally, or alternatively, the pharmacy may have to set up custom integrations with certain clearinghouses and/or other vendors to further assist with processing medical transactions. However, these integrations may be controlled primarily by the clearinghouses and not allow for expansion of pharmacy programs to additional payers, thereby limiting the pharmacy's capabilities.

A method, apparatus, and computer program product are provided in accordance with an example embodiment in order to generate and process medical transactions utilizing data from various sources including a modified pharmacy benefits transaction and provide responses to the medical transactions in an efficient manner.

System Architecture

Figure 1:
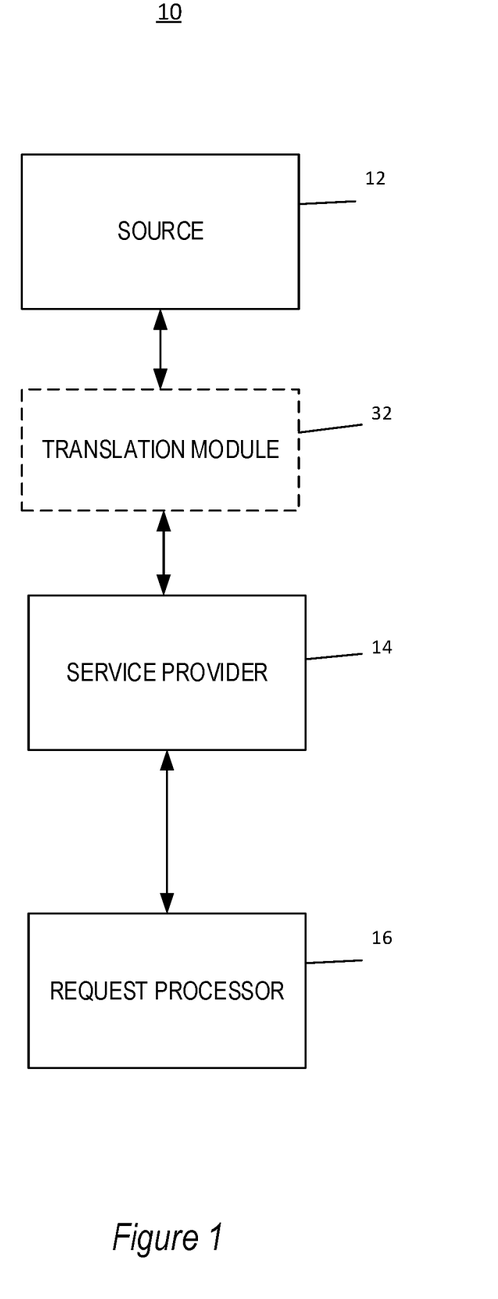
FIG. 1 is a diagram of a system configured in accordance with an example embodiment of the present invention.

By way of example, a system 10 that is configured to communicate and process medical transactions comprising data extracted from modified pharmacy benefits transactions is depicted in FIG. 1. As shown, a modified pharmacy benefits transaction may be provided by a source 12 (e.g., a pharmacy computer) and received by a translation module 32, which may be a part of the source 12 or, in some embodiments, a part of a service provider 14, such as a switch. After generating a medical transaction based at least on the modified pharmacy benefits transaction, the translation module 32 is configured to communicate with service provider 14, which in turn is configured to communicate with a request processor 16 and, in some embodiments, with other entities.

FIG. 1 is an overview of a system that can be used to analyze modified pharmacy benefits transactions and generate medical transactions. The source 12 may be associated with a pharmacy, such as an entity that may bill for and provide medication and/or treatments, for example, prescription and/or over-the-counter medications, immunizations, etc. While the exemplary source 12 may be frequently referenced herein as part of a pharmacy or pharmacy network, the source 12 may be associated with any other healthcare entity that may bill to pharmacy benefits plans.

The source 12 (e.g., a pharmacy computer) may be any processor-driven device that facilitates the processing of prescription benefit coverage inquiries made by physicians or clinical staff, and the communication of information associated with prescription benefit coverage inquiries to the service provider computer 14. The execution of the computer-implemented instructions by the source 12 and/or service provider 14 may form a special purpose computer or other particular machine that is operable to facilitate the processing of medical transactions made by pharmacists, pharmacy staff, and/or the like, and the communication of information associated therewith to a service provider 14 and/or request processor 16.

The service provider 14 may include, but is not limited to, a processor-driven device that is configured for receiving, processing, and fulfilling inquiries, responses, and/or requests from the source 12 and/or the request processor 16 (described below), relating to pharmacy benefits transactions, medical eligibility check requests, medical benefit claims, claims processing, billing, formatting and/or reformatting, other healthcare transactions, and/or other related activities. Additionally, or alternatively, the service provider computer 106 may be operable to facilitate the receipt, routing, and/or processing of medical transactions and/or associated responses amongst various components and/or subsystems such as, but not limited to, those depicted in FIG. 1.

In certain exemplary embodiments, the service provider 14 may be configured as or may comprise a switch or router that evaluates, processes, modifies, reformats, generates, and/or routes medical transactions and/or other healthcare transactions. For example, the service provider 14 may route medical transactions communicated from the source 12 (e.g., translation module 32) to a request processor 16, such as that associated with a clearinghouse, a medical benefits manager, an insurer, a Medicare or other government healthcare insurance program payor, or other payor, all of which are generally referenced herein as a payor.

Additionally, or alternatively, the service provider computer 14 may reformat medical transactions into another format (e.g., X12 or another medical benefits format) before routing the reformatted transaction to another party, such as a request processor 16. The request processor 16 may in turn route a response to the medical transaction to the service provider computer 106. The service provider 14 may then direct the response to the prescriber computer 12, translation module 32, or other associated entity.

In addition to receiving and storing information, the source 12 and/or service provider 14 may be further operable to access and/or be in communication with one or more suitable data storage devices, such as a database 30, for storing patient data, medical data, historical data, and/or other various data. In some embodiments, the database 30 comprises data relating to prescription transactions associated with one or more pharmacy computers 110 and/or medical transactions. Data, such as for example, historical data, may be provided by and/or stored in database 30 by a number of entities which may comprise the source 12 (e.g., one or more pharmacy computers), service provider 14, request processor 16, and/or other related entities.

The database 30 may be embodied by any of a variety of data storage devices such as a Network Attached Storage (NAS) device or devices, or as a separate database server or servers. The database 30 includes information accessed and stored by the processing circuitry 22 and/or translation module 32 to facilitate the operations of the source 12 and/or service provider 14. For example, the database 30 may comprise a series of tables configured to store information such as patient data, insurance plan data, and/or the like.

The service provider 14 may transmit responses regarding the medical transactions to the source 12 (e.g., translation module 32). For example, the service provider 14 may notify the source 12 of and/or provide a response related to a medical transaction from the request processor 16. However, according to some example embodiments, a response from the request processor 16 may not be received, and the service provider 14 may provide a transaction identifier, as described in further detail below. In this regard, a message or other notification may be appended to or included in the response transmitted to the source 12.

The example system of FIG. 1 described above is provided merely as an example and it will be appreciated that the example embodiments provided herein may be implemented as or employed by any number of system architectures. Some modifications may be made to certain embodiments. It will be further appreciated that any of the components of FIG. 1 are configured to communicate over a network, or network(s), as described in further detail herein.

Figure 2:
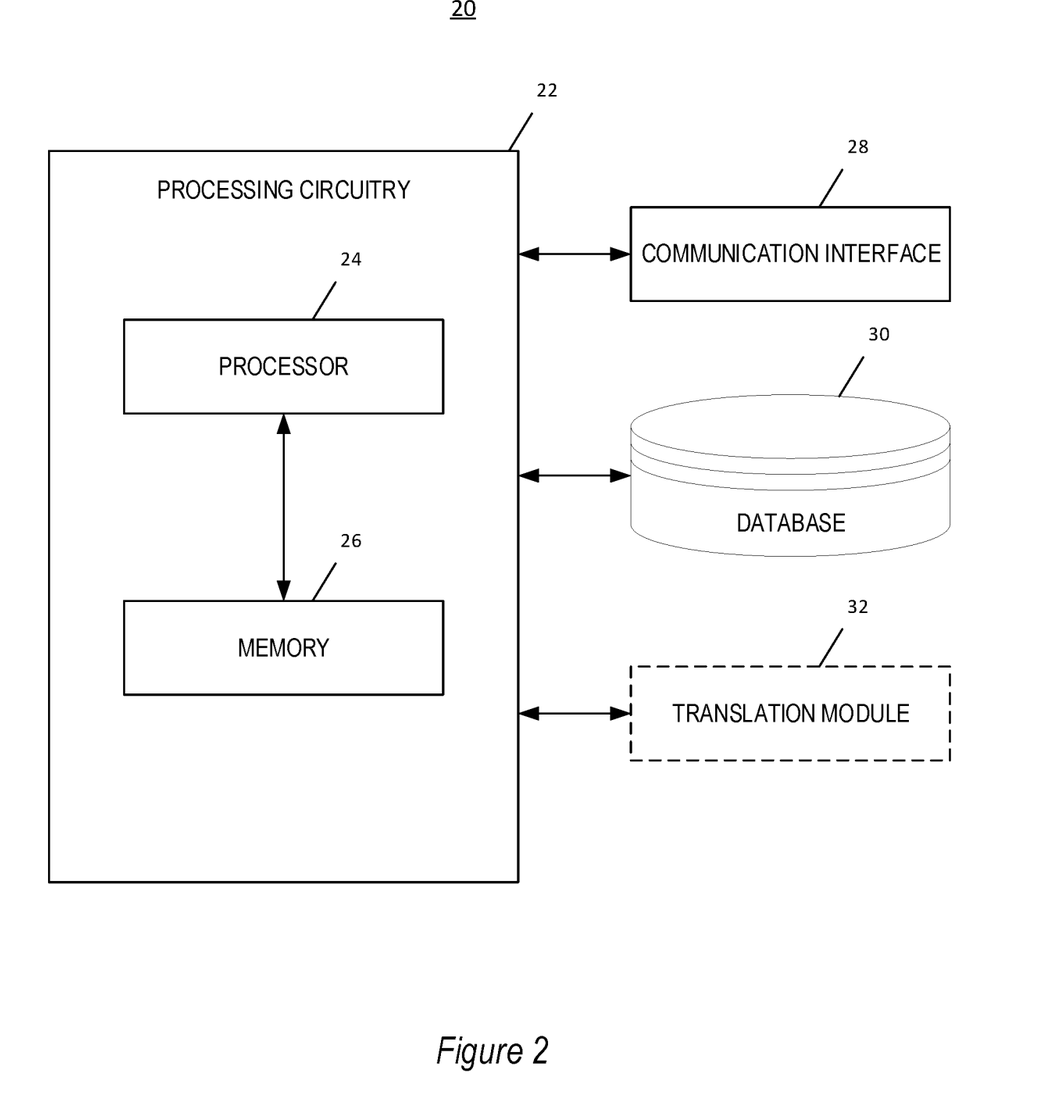
FIG. 2 is a block diagram of a computing device that may be specifically configured in accordance with an example embodiment of the present invention.

The source 12 and/or service provider 14 may be configured in various manners, but, in embodiment, the source 12 and/or service provider 14 includes an apparatus 20 configured to generate and process medical transactions and may be embodied as shown in FIG. 2. In this regard, the apparatus of the source 12 and/or service provider 14 may be embodied by any of various computing devices, such as servers, computer workstations or the like, and may include or otherwise be in communication with a processing system including, for example, processing circuitry 22 that is configurable to perform actions in accordance with example embodiments described herein. The processing circuitry may be configured to perform data processing, application execution and/or other processing and management services. The processing circuitry may include a processor 24 and memory 26 that may be in communication with or otherwise control a communication interface 28, a database 30, and a translation module 32. The apparatus may also include the communication interface, database, and/or translation module 32 as shown in FIG. 2, or the communication interface, database and/or the translation module may be separate from, but in communication with, the apparatus.

It should be noted that the components, devices, and elements illustrated in and described with respect to FIG. 2 may not be mandatory and thus some may be omitted in certain embodiments. For example, FIG. 2 illustrates a translation module 32, as described in more detail below, which may be optional in any of the source 12 or service provider 14 as indicated by the dashed border, as the translation module may, instead, be embodied by the other of the source or service provider or may be a distinct component relative to the source and the service provider. Additionally, some embodiments may include further or different components, devices, or elements beyond those illustrated in and described with respect to FIG. 2.

In some example embodiments, the memory 26 may include one or more non-transitory memory devices such as, for example, volatile and/or non-volatile memory that may be either fixed or removable. In this regard, the memory 26 may comprise a non-transitory computer-readable storage medium. It will be appreciated that while the memory 26 is illustrated as a single memory, the memory 26 may comprise a plurality of memories. The plurality of memories may be embodied on a single computing device or may be distributed across a plurality of computing devices. The memory 26 may be configured to store information, data, applications, computer program code, instructions and/or the like for enabling apparatus 20 to carry out various functions in accordance with one or more example embodiments. For example, when apparatus 20 is implemented as a source 12 or service provider 14, memory 26 may be configured to store computer program code for performing corresponding functions thereof, as described herein according to example embodiments.

The memory 26 may be further configured to buffer input data for processing by the processor 24. Additionally, or alternatively, the memory 26 may be configured to store instructions for execution by the processor 24. In some embodiments, the memory 26 may include one or more databases, such as database 30, that may store a variety of files, contents, or data sets, such as but not limited to historical data. Among the contents of the memory 26, applications may be stored for execution by the processor 24 to carry out the functionality associated with each respective application. In some cases, the memory 26 may be in communication with one or more of the processor 24, communication interface 28, and/or translation module 32 for passing information among components of apparatus 20.

The processor 24 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor may be configured to execute instructions stored in the memory 26 or otherwise accessible to the processor. As such, whether configured by hardware or by a combination of hardware and software, the processor may represent an entity (e.g., physically embodied in circuitry—in the form of processing circuitry) specifically configured to perform operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the operations described herein.

The communication interface 28 may include one or more interface mechanisms for enabling communication with other devices and/or networks. In some cases, the communication interface 28 may be any means such as a device or circuitry embodied in either hardware, or a combination of hardware and software that is configured to receive and/or transmit data from/to a network and/or any other device or module in communication with the processing circuitry 210. By way of example, the communication interface 28 may be configured to enable communication amongst any of source 12, service provider 14, request processor 16, and/or apparatus 20 over a network. Accordingly, the communication interface 28 may, for example, include supporting hardware and/or software for enabling wireless and/or wireline communications via cable, digital subscriber line (DSL), universal serial bus (USB), Ethernet, or other methods.

The network, such as the network in which the system of FIG. 1 or components thereof or components described herein may operate, (e.g., source 12, service provider 14, request processor 16, apparatus 20, and/or the like) may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

In an embodiment in which the apparatus 20 is embodied by a source 12 (e.g., a computing device associated with a pharmacy) and/or service provider 14, the apparatus 20 may comprise additional circuitry for carrying out operations associated with generating and processing medical transactions. For example, the apparatus 20 may comprise a translation module 32. Thus, the translation module 32 may be embodied by the source 12, or by the service provider 14 or may be distributed between and embodied by a combination of both the source and the service provider. Still further, the translation module 32 of another embodiment may be separate from, but in communication with the source 12 and the service provider 14. The translation module 32 may comprise the processing circuitry 22 or otherwise be in communication with the processing circuitry and may also comprise one or more instructions or predefined functions for directing the processing circuitry 22 to carry out operations associated with the translation module 32. In an embodiment, the translation module 32 may comprise one or more predefined functions and/or commands for receiving data, such as receiving pharmacy benefits transactions and/or modified pharmacy benefits transactions, medical transactions, responses to pharmacy benefits transactions, modified pharmacy benefits transactions, and/or medical transactions, and/or any other data. In some embodiments, the translation module 32 may comprise may comprise one or more predefined functions and/or commands for parsing and extracting data from a transaction. In some embodiments, the translation module 32 may further comprise one or more predefined functions and/or commands for generating and formatting a medical transaction. The examples provided above are just some of the functionalities that may be associated with the translation module 32, and it is to be appreciated that the translation module 32 may comprise further commands, functions, and/or other functionalities associated with the processing of pharmacy benefits transactions and/or medical transactions.

Figure 3:
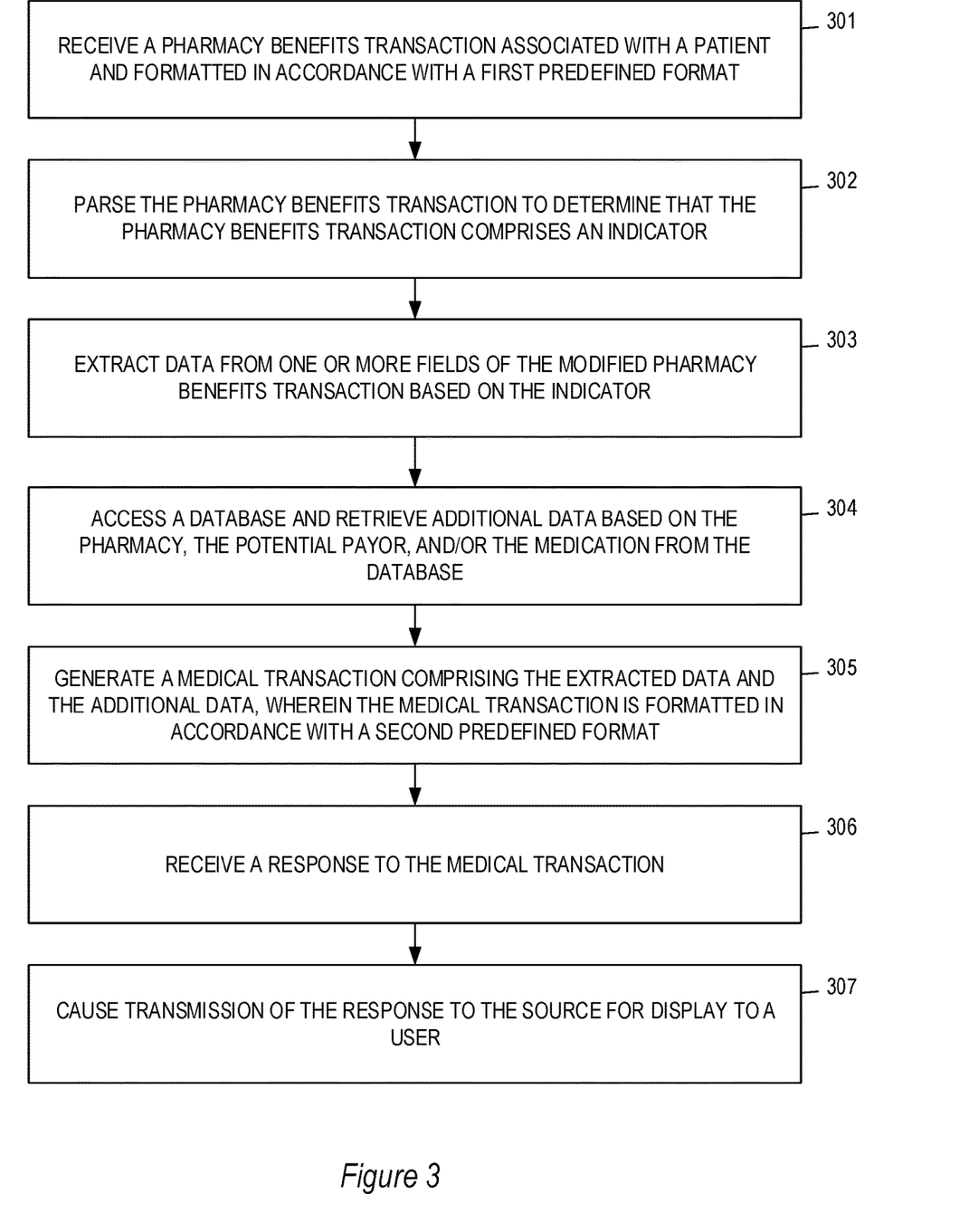
FIG. 3 is a flow chart illustrating operations performed in accordance with an example embodiment of the present invention.

The operations performed by the apparatus 20 embodied by the source 12 (e.g., a pharmacy computer) and/or service provider 14 are depicted in an example embodiment in FIG. 3. As shown, the apparatus of an example embodiment, such as the communication interface 28, translation module 32, processing circuitry 22 or the like, is configured to receive a pharmacy benefits transaction from a source 12 as shown in block 301 of FIG. 3. Although different types of electronic messages or transactions may be received depending upon the application, the received transaction may be a pharmacy benefits transaction, such as a prescription claim request or the like, and may be generated by a pharmacy (e.g., a pharmacy management system) and is directed to the translation module 32 for processing prior to submission to a service provider 14 and/or request processor 16 for further processing. In this embodiment, the pharmacy benefits transaction may comprise information that identifies a patient, a medication, product, or treatment, a healthcare provider (a prescriber of the treatment, the pharmacy, or both), and/or a benefit plan, insurer, or government-funded payor for the patient.

In some embodiments, the pharmacy benefits transaction may be formatted in accordance with a first predefined format. Although the first predefined format may vary from one electronic transaction to another, the pharmacy benefits transaction of an example embodiment may be formatted in accordance with the National Council for Prescription Drug Programs (NCPDP) communications standard that is utilized in conjunction with the submission of pharmacy transactions, such as prescription claim requests. As described above, pharmacy transactions conventionally utilize the NCPDP communications standard, which contributes to pharmacies' challenges to effectively process and submit medical transactions, challenges which are solved by embodiments detailed further herein.

Although the pharmacy may initially submit a medical eligibility request or a medical benefits claim pursuant to a medical benefits plan, the method, apparatus and computer program product will be described in conjunction with an embodiment in which the pharmacy initially submits an eligibility request or a claim pursuant to a pharmacy benefits plan and only submits a medical eligibility request or a medical benefits claim after a pharmacy benefits plan has issued a rejection and/or indication of no coverage for the particular medication, treatment, etc. In this example embodiment, the pharmacy benefits transaction may be transmitted to the translation module 32 by a source 12 (e.g., a pharmacy computing device at a pharmacy) after the pharmacy benefits transaction had been rejected by a request processor (e.g., a prescription claims processor) or other third party. In this regard, for example, a pharmacist may have previously submitted the pharmacy benefits transaction, which may be a prescription claim for a particular medication for a patient, to a prescription claims processor and, in response, may have received a rejection from the prescription claims processor, such as a denial of coverage under the patient's prescription plan, or the like.

At operation 302, the apparatus of an example embodiment, such as the translation module 32, processing circuitry 22 or the like, is configured to parse the pharmacy benefits transaction to determine that the pharmacy benefits transaction comprises an indicator. For example, the indicator may comprise data indicating that the pharmacy benefits transaction is a modified pharmacy benefits transaction (e.g., comprises an indicator and/or additional data as described below) is to be processed as a particular medical transaction. In this regard, upon receiving a rejection of the pharmacy benefits transaction at the source 12 (e.g., the pharmacy), a pharmacist or the like may modify the pharmacy benefits transaction to submit the pharmacy benefits transaction as a medical transaction, for example, to determine if a particular medication or treatment associated with the pharmacy benefits transaction is billable to a medical benefits plan, and/or if the patient associated with the pharmacy benefits transaction is eligible to receive medical benefits. In another embodiment, the source 12 may be configured to automatically cause transmission of an indicator associated with the pharmacy benefits transaction upon receiving a rejection of the pharmacy benefits transaction without manual intervention by a pharmacist or the like. In either case, the source 12 may be configured, via processing circuitry 22 or the like, to cause transmission of an indicator associated with the pharmacy benefits transaction. For example, the source 12 may cause transmission of the indicator to the translation module 32 along with the pharmacy benefits transaction such that the pharmacy benefits transaction comprises the indicator, such as populating a predefined indicator field. In another embodiment, the source 12 may cause transmission of the indicator to the translation module 32 separately from the pharmacy benefits transaction.

In either case, the indicator may comprise data indicating that the pharmacy benefits transaction is a modified pharmacy benefits transaction and is to be processed as a particular medical transaction. In an embodiment, the indicator may comprise data indicating that the modified pharmacy benefits transaction is to be processed as a medical eligibility check request, herein referred to as a medical eligibility check indicator. In another embodiment, the indicator may comprise data indicating that the modified pharmacy benefits transaction is to be processed as a medical benefit claim, herein referred to as a medical benefits claim indicator.

At operation 303, the apparatus of an example embodiment, such as the translation module 32, the processing circuitry 22 or the like, is configured to extract data from one or more fields of the modified pharmacy benefits transaction based on the indicator. For example, the modified pharmacy benefits transaction may comprise a plurality of data fields comprising data associated with a particular patient and/or other healthcare data. Some data fields may comprise data required to process the pharmacy benefits transaction, such as via a prescription claims processor or the like. Data from these same data fields may also be required to process the particular medical transaction associated with the indicator. Additionally, some data fields in the modified pharmacy benefits transaction may comprise data not necessarily required to process the pharmacy benefits transaction and therefore may not be utilized by a prescription claims processor or the like when processing the pharmacy benefits transaction (e.g., via a prescription claims processor). However, these fields that are unused by a prescription claims processor may comprise additional data that may be needed in order to process a medical transaction, such as a medical eligibility check request, a medical benefit claim, and/or the like. In an embodiment, these unused fields may have been pre-filled with corresponding data at an earlier time, such as prior to submitting the pharmacy benefits transaction to a prescription claims processor even though the prescription claims processor will not utilize the data that fills the unused fields. In another embodiment, prior to causing transmission of the modified pharmacy benefits transaction along with the indicator indicating that the modified pharmacy benefits transaction is to be processed as a medical transaction, the unused fields may be populated (e.g., automatically or manually by a pharmacist) prior to transmission based on the indicator, such as following denial by the prescription claims processor. In this regard, based on the type of indicator determined to be associated with the modified pharmacy benefits transaction, the apparatus 20 may extract data from the plurality of fields in accordance with data required by the particular medical transaction to be processed.

As one example, in an instance in which the indicator is determined to be a medical eligibility check indicator, examples of data fields that may be conventionally utilized in a pharmacy benefits transaction and extracted from the modified pharmacy benefits transaction to be also utilized in a medical eligibility check request may include any one or more of Transaction Identifier (ID), Subscriber Last Name, Subscriber First Name, Subscriber Date of Birth (DOB), Patient Relationship Code, Submitted Date, and/or other data fields. These data fields are provided by way of example and not of limitation and other data fields may be utilized in addition to or instead of the data fields listed above.

In some embodiments, additional data may be required for a medical transaction that is not traditionally included in pharmacy benefit transactions (e.g., NCPDP-formatted transactions). For example, this data may be included in other fields that are present but are not traditionally populated in a pharmacy benefit transaction. In some embodiments, as described above, this additional data may be pre-populated (e.g., by source 12) along with inclusion of the indicator. For example, at a time at which a pharmacist decides to modify and submit the pharmacy benefits transaction as a medical transaction and associate the pharmacy benefits transaction with a particular indicator (e.g., a medical eligibility check indicator and/or a medical benefit claim indicator), based on the type of indicator, the modified pharmacy benefits transaction may be pre-populated to include additional data required by the type of medical transaction indicated by the indicator.

In some embodiments, one or more data fields of the modified pharmacy benefits transaction may be repurposed to include different data than intended (e.g., when processing via a prescription claims processor) based on the associated indicator. In this regard, one or more data fields of a modified pharmacy benefits transaction that are populated with different data when the transaction is to be forwarded to a prescription claims processor may be repurposed and different data may be included in the fields when the transaction is to be treated as a medical transaction. In some embodiments, the population of this data into the repurposed fields may be done automatically (e.g., by source 12) or manually, such as via a pharmacist at source 12. In this regard, the translation module 32, such as the processing circuitry 22, may extract data in the repurposed fields to be included in the particular medical transaction.

At operation 304, the apparatus of an example embodiment, such as the translation module 32, the processing circuitry 22 or the like, is configured to access a database 30 and retrieve additional data from the database. For example, additional data that may be required to be included in the medical transaction that may not be present in the modified pharmacy benefits transaction may be stored in memory accessible by the translation module 32, such as in database 30. As one example, in an instance in which the medical transaction is a medical benefit check request, the translation module 32 may access the database 30 in order to retrieve data comprising a Payer ID to be included in the medical eligibility check request. In this regard, the Payer ID may be required to be included in the medical eligibility check request but may not be required by the pharmacy benefits transaction and therefore may not be present in the original pharmacy benefits transaction. However, a Payer Name may be present in the modified pharmacy benefits transaction. In this regard, the translation module 32 may access the database and retrieve the correct Payer ID based on data in the pharmacy benefits transaction (e.g., Payer Name).

The additional data that is retrieved from the database may be based at least in part on one or more of a pharmacy with which the source 12 is associated, a potential payor of the medical transaction or a medication that is a subject of the medical transaction. In an example embodiment, the apparatus of an example embodiment, such as the translation module 32, the processing circuitry 22 or the like, is configured to define one or more business rules. The business rule(s) serve to define the additional data that is to be retrieved from the database based at least in part on one or more of a pharmacy with which the source is associated, a potential payor of the medical transaction or a medication that is a subject of the medical transaction. In some embodiments, the business rule(s) to be utilized to define the additional data that is to be retrieved from the database may be based upon the pharmacy with which the source is associated, such that a first pharmacy or a first chain of pharmacies may cause one or more first business rules to be utilized to define the additional data that is to be retrieved from the database, while a second pharmacy or a second chain of pharmacies may cause one or more second business rules, different than the first business rule(s), to be utilized to define the additional data that is to be retrieved from the database. The data that is retrieved from the database may relate to the patient, the pharmacy, a chain of pharmacies, the medication (such as based on the National Drug Code (NDC) of the medication), the payor or charges for services rendered, or may be other types of data retrieved from the database.

In this regard, the translation module 32 may be configured to retrieve data for insertion into the medical benefits transaction based on specific match criteria (e.g., a match key) in the modified pharmacy benefits transaction. Example match keys may include, but is not limited to, National Provider Identifier (NPI), NDC, Therapeutic Class, Payer, and/or historical data related to a patient's prior history for medical transactions (e.g., historical data stored in database 30), and any combination thereof. Once matched, identified data in database 30 may be retrieved for insertion into a medical transaction.

Additional examples of data that translation module 32 may access the database 30 in order to retrieve in an instance in which the medical transaction is a medical benefit check request may include one or more of a Patient ID, Subscriber Middle Name, Subscriber Name Suffix, Subscriber Patient Gender, Dependent Patient Gender, Subscriber Member ID, Payer, Dependent Last Name, Dependent First Name, Dependent Name Suffix, and/or Dependent Member ID.

After having extracted data from one or more fields of the modified pharmacy benefits transaction and retrieved additional data from the database, the apparatus of an example embodiment, such as the translation module 32, the processing circuitry 22 or the like, may be configured to determine whether the extracted data and the additional data includes sufficient data required for generation and/or effective processing of a medical transaction. In some cases, one or more fields of data may be absent in both the modified pharmacy benefits transaction and the database 30 and therefore not readily available for inclusion in a medical transaction. In an instance in which it is determined that the extracted data and/or the additional data does not include sufficient data required for generation of a medical transaction, the apparatus 20 may generate an electronic message and cause transmission of the electronic message to the source 12. In some embodiments, the electronic message may comprise an indication of a rejection of the modified pharmacy benefits transaction as a medical transaction and/or comprise an indication of one or more missing data fields that are required to generate and/or effectively process the medical transaction. In this regard, a user (e.g., a pharmacist, staff, or the like) may review the information provided in the electronic message at the source 12 in gather the necessary information to provide back to the translation module 32. By generating the rejection by the apparatus 20, such as the translation module 32, the processing circuitry 22 or the like, a technical advantage may be provided by avoiding an exchange of messages with a medical claims processor, thereby conserving both network and processing resources.

In an instance in which the extracted data and the additional data are determined to include sufficient data required for generation of a medical transaction, the translation module 32 may proceed with generating the medical transaction. At operation 305, the apparatus of an example embodiment, such as the translation module 32, the processing circuitry 22 or the like, is configured to generate a medical transaction comprising the extracted data and the additional data. In an embodiment, the medical transaction may be formatted in accordance with a second predefined format, different than the first predefined format described above with respect to the modified pharmacy benefits transaction. In some embodiments, the second predefined format may be a specialized format, e.g., a proprietary format defined by the service provider 14 and/or the source 12, configured to be efficiently translated and/or reformatted into another format, e.g., an X12 format, based on a particular destination (e.g., a type of request processor that will process the medical transaction). The medical transaction may be a medical eligibility check request, a medical benefit claim, and/or the like.

After having generated the medical transaction, the apparatus 20, such as the translation module 32, the processing circuitry 22, the communication interface 28 or the like, is configured to cause transmission of the medical transaction. In some embodiments, the apparatus 20 may cause transmission of the medical transaction to the service provider 14. In this regard, the service provider 14 may be configured via the communication interface 28 or the like, to receive the medical benefits transaction.

In some embodiments, after the service provider 14 has received the medical transaction, the service provider 14 may be configured to process the medical transaction and further, may cause transmission of the medical transaction to a request processor 16 for processing. In some embodiments, the processing of the medical transaction by the service provider 14 may comprise converting the medical transaction into another format suitable to processing by a request processor 16. For example, the service provider 14, having received the medical transaction in the second predefined format (e.g., the specialized format as described above), may convert the medical transaction to a different format suitable for processing by a request processor, such as a format typically utilized in conjunction with medical claim processing, such as X12 or the like. After conversion, the service provider 14 may cause transmission of the converted medical transaction to the request processor 16.

At operation 306, the apparatus of an example embodiment, such as the translation module 32, the processing circuitry 22, communication interface 28 or the like, is configured to receive a response to the medical transaction. For example, in response to the transmission of the medical transaction (e.g., to a service provider 14) the apparatus 20 may receive a response to the medical transaction. In this regard, after service provider 14 has caused transmission of the converted medical transaction to the request processor 16 as described above, the service provider 14 may receive a response to the converted medical transaction from the request processor 16. In some embodiments, the service provider 14 may process the response prior to causing transmission of the response to translation module 32. For example, the service provider may convert the response to another format, construct a separate response comprising only a portion of data from the response received from the request processor 16, and/or other processing. The response to the medical transaction may differ depending on the type of medical transaction.

For example, in an instance in which the medical transaction is a medical eligibility check request, the response to the medical eligibility check request may comprise an indication of patient eligibility for the patient associated with the medical eligibility check request. The indication of patient eligibility may comprise an indication of a status such as eligible, not eligible, unknown, or the like. In some embodiments, the response may comprise a transaction identifier as detailed further below. In an instance in which the medical transaction is a medical eligibility check request, the response to the medical eligibility check request may be received in or near real-time following transmission of the medical eligibility check request (e.g., from translation module 32 to the service provider 14).

Pharmacies may interact with patients in-person, such as during a patient's visit to a pharmacy to fill a prescription, or remotely, such a via a telehealth platform. In either scenario, the patients may sometimes need to fill the prescription urgently, as the patient may be ill and in immediate need of the medication and/or treatment related to the prescription. Likewise, the pharmacy may need to assist a multitude of patients daily and therefore need to assist each patient efficiently and in a timely manner. Thus, it may be important for the source 12 (e.g., a pharmacy) to receive a prompt response to the medical eligibility check request in order to provide the patient with an answer to a medical eligibility check request. In some embodiments, such as embodiments in which the medical transaction is a medical eligibility check request and the translation module 32 is embodied by the service provider 14, the apparatus 20 such as the translation module 32, may be further configured to configure a timeout value to be associated with the medical eligibility check request. In some embodiments, the timeout value may be a predefined value stored in memory (e.g., memory 26) and associated with all medical eligibility check requests processed by service provider 14. In this regard, the apparatus 20 need not configure a separate timeout value in each instance a medical eligibility check request is received.

The timeout value may represent a maximum amount of time in which the service provider 14 is expected to receive a response to the medical eligibility check request from the request processor 16. For example, technical or other issues may arise at the request processor 16 such that a response to the medical eligibility check request may be delayed. In this regard, the apparatus of an example embodiment, such as the translation module 32, processing circuitry 22, and/or the like, may be configured to monitor for receipt of a response associated with the medical eligibility check request, and, in an instance in which it is determined that a response to the medical eligibility check request has not been received for a time period exceeding the timeout value, generate a transaction identifier for the medical eligibility check request. Alternatively, the apparatus 20 of another example embodiment may not be configured to monitor for violation of the timeout value and then generate a transaction identifier, but, instead, the apparatus, such as the translation module 32, the processing circuitry 22 or the like, of this other example embodiment may be configured to receive a transaction identifier, such as from the service provider 14, in an instance in which the timeout value has been exceeded. In either embodiment, the apparatus of an example embodiment, such as the translation module 32, processing circuitry 22 and/or communication interface 28, may be further configured to cause transmission of the transaction identifier to the source 12 for presentation to a user (e.g., a pharmacist, patient, pharmacy staff, and/or the like). For example, in some embodiments, the response to the medical eligibility check request may comprise the transaction identifier. The transaction identifier may comprise numerical, text, and/or string data (e.g., a unique code) and may be based on data associated with the medical eligibility check request and serve to identify the particular transaction of the medical eligibility check request between the service provider 14 and the request processor 16 and thus be associated with the particular medical eligibility check request. Once received at the source 12, the transaction identifier may be used by the pharmacist and/or patient to retrieve information about the response to the particular medical eligibility check request via a web portal or the like associated with the service provider 14 and/or source 12 at a later time. For example, the transaction identifier may be input to a web portal in order to view a result of the medical eligibility check request.

By generating and causing transmission of the transaction identifier in an instance in which it is determined that a response to the medical eligibility check request has not been received for a time period exceeding the timeout value, the source 12 (e.g., pharmacy) may be better equipped with information to provide to a patient regarding the medical eligibility check request. For example, when a transaction identifier is received as a response to the medical eligibility check request in lieu of a response comprising an indication of eligibility, the pharmacy may be made aware that the request processor 16 is currently experiencing issues in processing medical eligibility check requests and thus not attempt to transmit one or more additional medical eligibility check requests. For instance, if the request processor 16 is currently experiencing issues with processing medical eligibility check requests and the source 12 were to not receive any sort of response after submitting the medical transaction, a user at source 12 (e.g., a pharmacist) may experience confusion and be caused to re-submit the medical transaction one or more times, thereby further unnecessarily increasing the load upon the network, source 12, service provider 14, and/or request processor 16.

In another embodiment, such as in an instance in which the medical transaction is a medical benefits claim, the response to the medical benefits claim may comprise an indication acceptance of the medical benefits claim by a request processor. In other words, the response may indicate that the medical benefits claim was accepted for submission to a clearinghouse and/or medical plan. For example, a response to the medical benefits claim comprising approval or denial information may not be readily available as the request processor 16 may process medical benefits claims as a batch process (e.g., a nightly batch) and not in or near real-time such as with medical eligibility check requests. In this regard, the response received may comprise an indication that the medical benefits claim was accepted at the request processor 16 such that the medical benefits claim is in queue and will be processed in a future batch, or alternatively may comprise an indication that the medical benefits claim was not accepted at the request processor 16. In addition to the indication of acceptance/denial, in some embodiments, the response to the medical benefits claim may comprise a transaction identifier associated with the medical benefits claim to serve as a reference between organizations (e.g., the source 12, service provider 14, and/or request processor 16).

Figure 4:
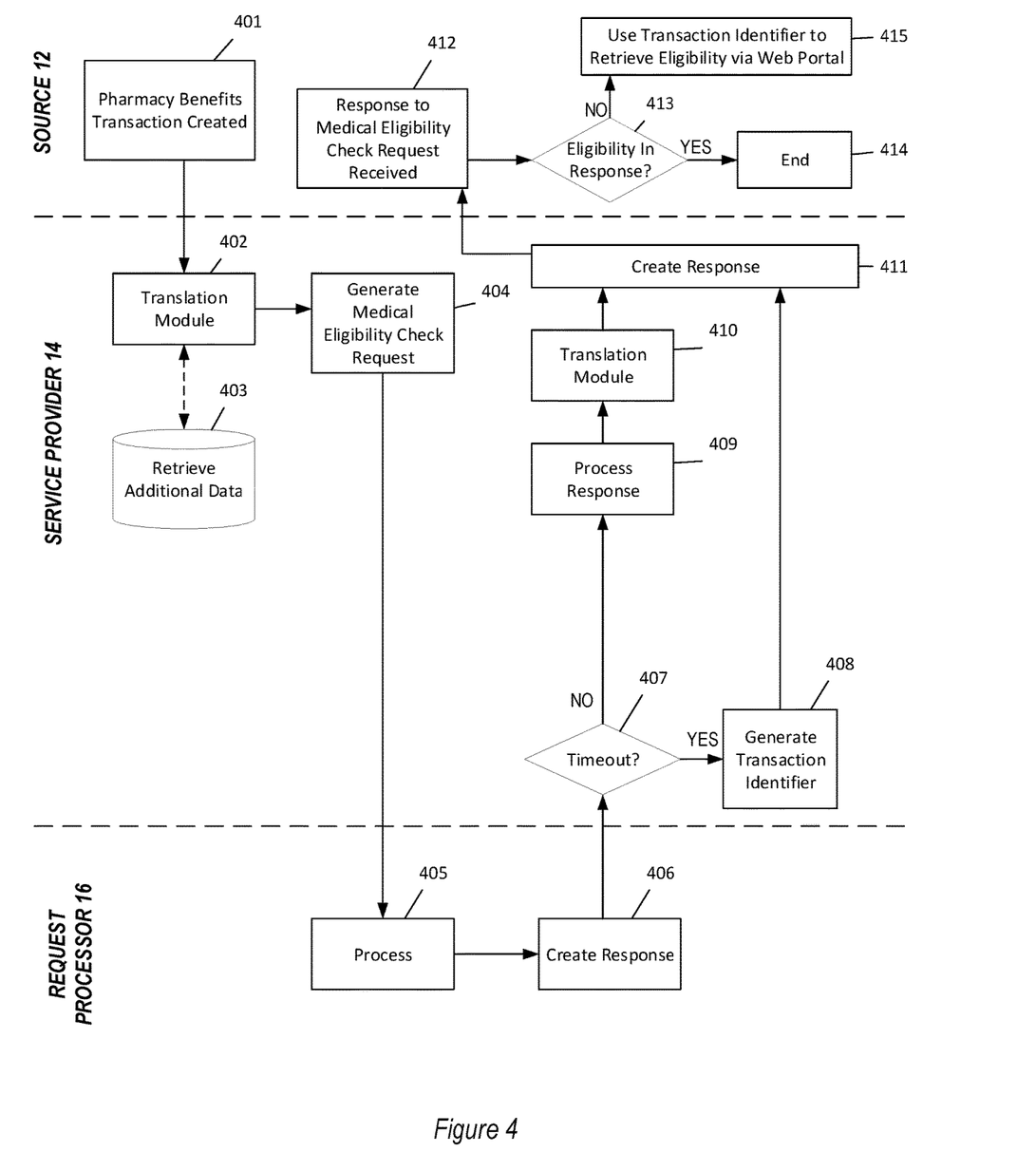
FIG. 4 is a signal flow diagram illustrating operations performed in conjunction with an example embodiment of the present invention.

FIG. 4 is a signal flow diagram further illustrating operations performed by the source 12, translation module 32, service provider 14, and request processor 16 in conjunction with an example embodiment, such as in an instance in which a modified pharmacy benefits transaction is to be submitted as a medical eligibility check request. As described above, a source 12 (e.g., a pharmacy) may create a pharmacy benefits transaction for a particular patient, as seen in step 401. For example, upon receiving a rejection of the pharmacy benefits transaction, such as by a prescription claims processor, the pharmacy benefits transaction may be modified and may be subsequently submitted as a medical eligibility check request. As described above, the medical eligibility check request may comprise a medical eligibility check indicator.

The modified pharmacy benefits transaction may be received by the translation module 32, such as processing circuitry 22, at step 402, similarly to operation 301 as described above in conjunction with FIG. 3. Though the translation module 32 is illustrated as a component of the service provider 14 in FIGS. 4 and 5, it is to be appreciated that the translation module 32 may be a component of and/or embodied by the source 12 in some embodiments. Further, in some embodiments, the translation module 32 may be a standalone component, separate from both the source 12 and service provider 14, or may alternatively be distributed between the source and the service provider.

After the modified pharmacy benefits transaction is received by the translation module 32 at step 402, the translation module 32, such as processing circuitry 22, may parse the modified pharmacy benefits transaction to determine that the modified pharmacy benefits transaction comprises an indicator, similarly to operation 302 as described above in conjunction with FIG. 3. Further, the translation module, such as processing circuitry 22, may extract data from one or more fields of the modified pharmacy benefits transaction based on the indicator, similarly to operation 303 as described above. In the present embodiment of FIG. 4, for example, the translation module 32, such as processing circuitry 22, may determine that the modified pharmacy benefits transaction comprises a medical eligibility request indicator.

The translation module 32, such as processing circuitry 22, may, at step 403, access a database (e.g., database 30) and retrieve additional data from the database. As described above in conjunction with operation 304 of FIG. 3, additional data that may be required to be included in the medical eligibility check request that may not be present in the modified pharmacy benefits transaction may be stored in memory accessible by the translation module 32, such as in database 30.

At step 404, after having extracted data from the modified pharmacy benefits transaction and retrieved additional data from database 30, the translation module 32, such as processing circuitry 22, may generate a medical eligibility check request comprising the extracted data and the additional data and formatted in accordance with a second predefined format, as described above with reference to operation 305 of FIG. 3.

At step 405, the medical eligibility check request may be transmitted to the request processor 16. Prior to transmission, the medical eligibility check request may be converted and/or reformatted (e.g., by the service provider 14) to a different format suitable for processing by the request processor 16, such as a format typically utilized in conjunction with medical eligibility check processing, such as X12 or the like.

The request processor 16 may then process the medical eligibility check request and, in some embodiments, create a response as seen in step 406. The request processor 16 may additionally be configured to cause transmission of the response to the service provider 14.

At step 407, as described above, the service provider 14 may monitor for receipt of a response associated with the medical eligibility check request, and, in an instance in which it is determined that a response to the medical eligibility check request has not been received for a time period exceeding the timeout value, generate a transaction identifier for the medical eligibility check request at step 408. In other embodiments, as described above, the translation module 32, such as processing circuitry 22, may be configured to monitor for receipt of a response and to generate a transaction identifier in an instance in which a response is not received for a time period exceeding the timeout value.

In an instance in which it is determined that a response to the medical eligibility check request has been received in a time period not exceeding the timeout value, the response may be further processed at step 409, e.g., by service provider 14. In this regard, the response may be transmitted to the translation module at step 410 and the apparatus of an example embodiment, such as the translation module 32, e.g., the processing circuitry 22, may be configured to format the response to be in accordance with a third predefined format associated with a pharmacy, different from both the first predefined format and the second predefined format. In this regard, the response may be formatted such that data of the response is viewable in a human-readable format (e.g., for display to one or more users at a pharmacy).

At step 411, the response may be generated in the third predefined format. As described above, in an instance in which the pharmacy benefits transaction comprises a medical eligibility check indicator and is thus processed as a medical eligibility check request, the response received from the request processor 16 may comprise an indication of eligibility and, at step 411, the response may be generated, such as by the translation module 32, e.g., the processing circuitry 22, in the third predefined format and comprise the indication of eligibility. In an alternative embodiment, in an instance in which the response to the medical eligibility check request was not received for a time period exceeding the timeout value, the response may be generated in the third predefined format, at step 411, and comprise the transaction identifier generated at step 408, with the response then being transmitted to the source 12.

At step 412, the source 12 may then receive the response such that a user (e.g., pharmacist, staff, patient, and/or the like) may then review the response received. As described above, when processing a medical eligibility check request, the response may be received in or near real-time. At step 413, the response may be reviewed and, in an instance in which the response comprises an indication of eligibility, the user may view the indication of eligibility, e.g., via a user interface or the like at the source 12 and the process may end at step 414. Alternatively, in an instance in which the response comprises a transaction identifier, at step 415, the user may use the transaction identifier to retrieve eligibility information when it becomes available at a later time via a web portal or the like.

Figure 5:
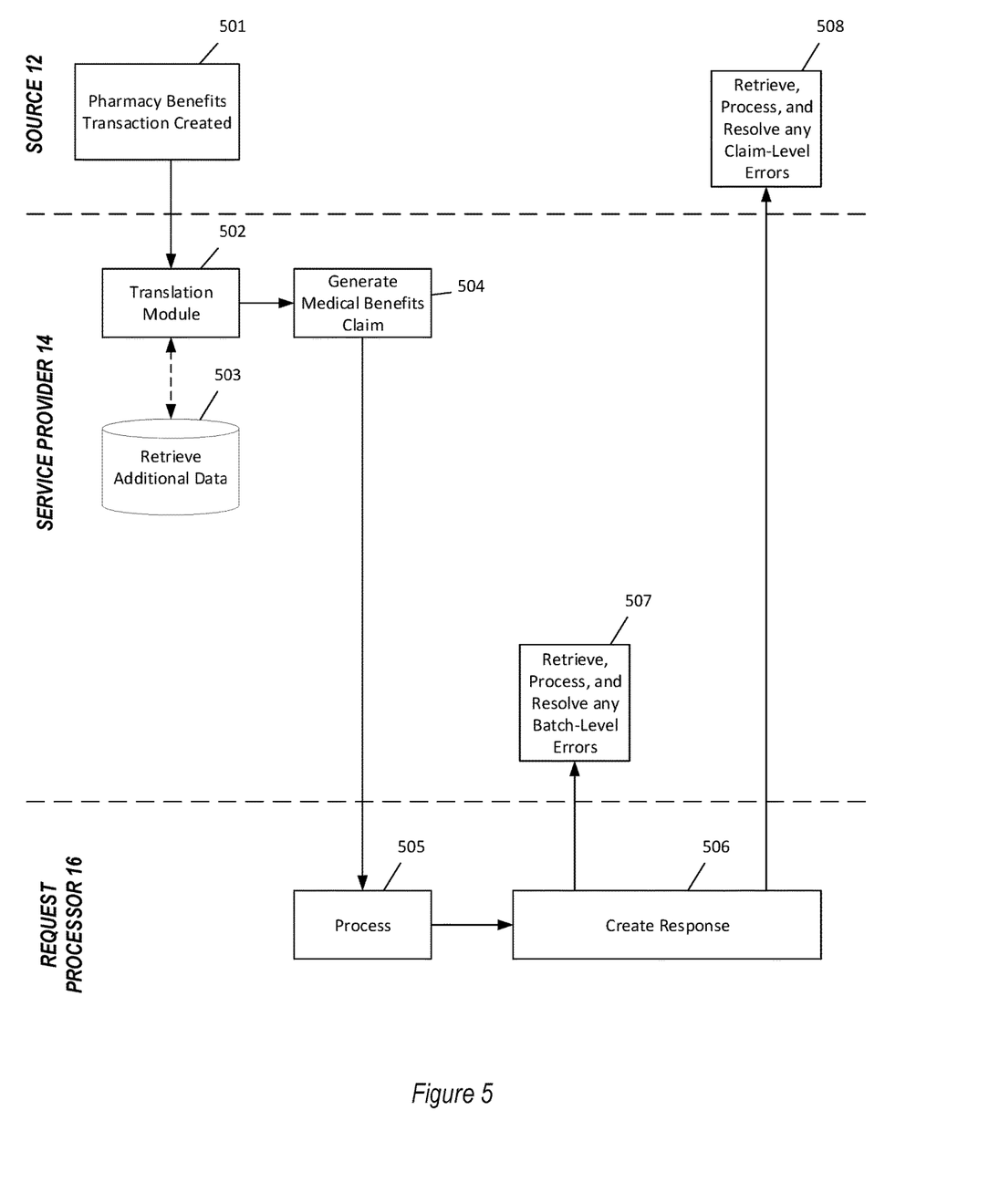
FIG. 5 is a signal flow diagram illustrating operations performed in conjunction with an example embodiment of the present invention.

FIG. 5 is a signal flow diagram further illustrating operations performed by the source 12, translation module 32, service provider 14, and request processor 16 in conjunction with an example embodiment, such as in an instance in which a modified pharmacy benefits transaction is to be submitted as a medical benefits claim. As described above, a source 12 (e.g., a pharmacy) may create a pharmacy benefits transaction for a particular patient, as seen in step 501. For example, upon receiving a rejection of the pharmacy benefits transaction, such as by a prescription claims processor, the pharmacy benefits transaction may be modified and subsequently submitted as a medical eligibility check request. As described above, the medical eligibility check request may comprise a medical eligibility check indicator.

The modified pharmacy benefits transaction may be received by the translation module 32, such as processing circuitry 22, at step 502, similarly to operation 301 as described above in conjunction with FIG. 3. After the modified pharmacy benefits transaction is received by the translation module 32 at step 502, the translation module 32, such as processing circuitry 22, may parse the modified pharmacy benefits transaction to determine that the pharmacy benefits transaction comprises an indicator, similarly to operation 302 as described above in conjunction with FIG. 3. Further, the translation module, such as processing circuitry 22, may extract data from one or more fields of the modified pharmacy benefits transaction based on the indicator, similarly to operation 303 as described above. In the present embodiment of FIG. 5, for example, the translation module 32, such as processing circuitry 22, may determine that the modified pharmacy benefits transaction comprises a medical benefits claim indicator.

The translation module 32, such as processing circuitry 22, may, at step 503, access a database (e.g., database 30) and retrieve additional data from the database. As described above in conjunction with operation 304 of FIG. 3, additional data that may be required to be included in the medical benefits claim that may not be present in the pharmacy benefits transaction may be stored in memory accessible by the translation module 32, e.g., the processing circuitry 22, such as in database 30.

At step 504, after having extracted data from the modified pharmacy benefits transaction and retrieved additional data from database 30, the translation module 32, such as processing circuitry 22, may generate a medical benefits claim comprising the extracted data and the additional data and formatted in accordance with a second predefined format, as described above with reference to operation 305 of FIG. 3. The medical benefits claim may then be transmitted to the request processor 16.

Prior to transmission, the medical eligibility check request may be converted and/or reformatted (e.g., by the service provider 14, such as the translation module 32, e.g., the processing circuitry 22) to a different format suitable for processing by the request processor 16, such as a format typically utilized in conjunction with medical benefits claim processing, such as X12 or the like. In some embodiments, as described above, the service provider 14 and/or translation module 32, such as processing circuitry 22, may cause transmission of a response comprising an indication of acceptance of the medical benefits claim by the request processor (e.g., to source 12).

The request processor 16 may then process the medical benefits claim as shown at step 505 and, in some embodiments, create a response as seen in step 506. As described above, medical benefits claims submitted to the request processor 16 may be handled in a batch, such as a nightly batch, and thus a response comprising an approval/denial of the medical benefits claim may not be readily available to the source 12 until the batch comprising the particular medical benefits claim has been processed by the request processor 16. Once processed, the request processor 16 may additionally be configured to cause transmission of the response to the service provider 14 and/or source 12.

In some embodiments, the response to the medical benefits claim generated and transmitted by the request processor 16 may comprise one or more errors associated with the medical benefits claim. In this regard, at step 507, the service provider 14 and/or translation module 32 may be configured to retrieve, process, and resolve any batch-level errors associated with the response prior to resubmittal of the medical benefits claim. At step 508, the source 12 and/or translation module 32, such as processing circuitry 22, may retrieve, process, and resolve any claim-level errors associated with the response.

As described above, a method, apparatus, and computer program product are provided in order to facilitate the efficient generation and submission of medical eligibility and medical claim data. As a result, submitters, such as pharmacies are alleviated from utilizing conventional, time-consuming alternatives. By providing a means for generation, submission, and processing of medical transactions, the method, apparatus, and computer program product of an example embodiment improves the efficiency and effectiveness of pharmacy workflows. Similarly, the method, computing device and computer program product of an example embodiment alleviates uncertainty and increased load on a network when submitting medical transactions by providing timely responses.

As noted above, FIG. 3 is a flowchart illustrating the operations performed by a method, apparatus and computer program product, such as apparatus 20 of FIG. 2, in accordance with one embodiment of the present invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory 26 of an apparatus employing an embodiment of the present invention and executed by a processor 24 of the computing device. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks. As such, the operations of FIG. 3, when executed, convert a computer or processing circuitry into a particular machine configured to perform an example embodiment of the present invention. Accordingly, the operations of FIG. 3 define an algorithm for configuring a computer or processing circuitry, e.g., processor, to perform an example embodiment. In some cases, a general purpose computer may be provided with an instance of the processor which performs the algorithm of FIG. 3 to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions. In some embodiments, certain ones of the operations above may be modified or further amplified and additional optional operations may be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method comprising:
receiving a modified pharmacy benefits transaction associated with a patient and a previously rejected pharmacy benefit transaction, and formatted in accordance with a first predefined format from a source;
parsing, by a processor, the modified pharmacy benefits transaction to determine that the modified pharmacy benefits transaction comprises a medical eligibility check indicator to transmit a medical transaction comprising a medical eligibility check;
extracting data from one or more fields of the modified pharmacy benefits transaction based on the medical eligibility check indicator to utilize in accessing a database for additional data to be utilized in generating the medical transaction;
in real-time or near real-time relative to the receipt of the modified pharmacy benefits transaction, accessing the database by the processor and retrieving additional data from the database indicative of a medical claims processor associated with a potential payor of the medical transaction;
generating, by the processor, the medical transaction in a second predefined format in accordance with the medical transaction to be processed by the medical claims processor by converting the extracted data into the second predefined format, wherein the second predefined format comprises at least an additional field not included in the rejected pharmacy benefit transaction;
transmitting the medical transaction to the medical claims processor determined from the database;
monitoring for receipt of a response associated with the medical transaction;
in an instance in which it is determined that the response to the medical transaction has not been received and a timeout occurs, generating an inclusive response including a transaction identifier and transmitting the inclusive response to the source for provision to a user; and
in an instance that the response is received and a timeout does not occur, generating an eligibility response comprising an indication of patient eligibility, formatting the eligibility response to be in accordance with a third predefined format associated with a pharmacy associated with the source from which the modified pharmacy benefits transaction was received, and causing transmission of the eligibility response to the source for provision to a user.

2. The computer implemented method of claim 1, wherein the timeout occurs if the response has not been received for a time exceeding the timeout value, and wherein the timeout does not occur if the response is received before the time exceeding the timeout value is reached.

3. The computer-implemented method of claim 1, wherein the modified pharmacy benefits transaction comprises a medical benefit claim indicator, wherein the medical transaction comprises a medical benefit claim, and wherein the response to the medical transaction comprises an indication of whether the medical benefit claim is accepted by the request processor.

4. The computer implemented method of claim 1, further comprising:
in an instance in which the extracted data and the additional data are determined to not include data required for generation of the medical transaction:
generating a rejection message comprising an indication of rejection of the modified pharmacy benefits transaction prior to transmission to a request processor; and
causing transmission of the rejection message to the source.

5. An apparatus comprising at least one processor and at least one memory including computer program code, the at least one memory and the computer program code configured to, with the processor, cause the apparatus to at least:
receive a modified pharmacy benefits transaction associated with a patient and a previously rejected pharmacy benefit transaction, and formatted in accordance with a first predefined format from a source;
parse the modified pharmacy benefits transaction to determine that the modified pharmacy benefits transaction comprises a medical eligibility check indicator to transmit a medical transaction comprising a medical eligibility check;
extract data from one or more fields of the modified pharmacy benefits transaction based on the medical eligibility check indicator to utilize in accessing a database for additional data to be utilized in generating the medical transaction;
in real-time or near real-time relative to the receipt of the modified pharmacy benefits transaction, access the database and retrieve additional data from the database indicative of a medical claims processor associated with a potential payor of the medical transaction;
generate the medical transaction in a second predefined format in accordance with the medical transaction to be processed by the medical claims processor by converting the extracted data into the second predefined format, wherein the second predefined format comprises at least an additional field not included in the rejected pharmacy benefit transaction;
transmit the medical transaction to the medical claims processor determined from the database;
monitor for receipt of a response associated with the medical transaction;
in an instance in which it is determined that the response to the medical transaction has not been received and a timeout occurs, generate an inclusive response including a transaction identifier and transmitting the inclusive response to the source for provision to a user;
in an instance that the response is received and a timeout does not occur, generate an eligibility response comprising an indication of patient eligibility, formatting the eligibility response to be in accordance with a third predefined format associated with a pharmacy associated with the source from which the modified pharmacy benefits transaction was received, and cause transmission of the response to the source for provision to a user.

6. The apparatus of claim 5, wherein the timeout occurs if the response has not been received for a time exceeding the timeout value, and wherein the timeout does not occur if the response is received before the time exceeding the timeout value is reached.

7. The apparatus of claim 5, wherein the modified pharmacy benefits transaction comprises a medical benefit claim indicator, wherein the medical transaction comprises a medical benefit claim, and wherein the response to the medical transaction comprises an indication of whether the medical benefit claim is accepted by the request processor.

8. The apparatus of claim 5, wherein the at least one memory and the computer program code are further configured to, with the processor, cause the apparatus to at least:
in an instance in which the extracted data and the additional data are determined to not include data required for generation of the medical transaction:
generate a rejection message comprising an indication of rejection of the modified pharmacy benefits transaction prior to transmission to a request processor; and
cause transmission of the rejection message to the source.

9. A computer program product comprising at least one non-transitory computer-readable storage medium having computer-executable program code instructions stored therein, the computer-executable program code instructions comprising program code instructions to:
receive a modified pharmacy benefits transaction associated with a patient and a previously rejected pharmacy benefit transaction and formatted in accordance with a first predefined format from a source;
parse the modified pharmacy benefits transaction to determine that the modified pharmacy benefits transaction comprises a medical eligibility check indicator to transmit a medical transaction comprising a medical eligibility check;
extract data from one or more fields of the modified pharmacy benefits transaction based on the medical eligibility check indicator to utilize in accessing a database for additional data to be utilized in generating the medical transaction;
in real-time or near real-time relative to the receipt of the modified pharmacy benefits transaction, access the database and retrieve additional data from the database indicative of a medical claims processor associated with a potential payor of the medical transaction or a medication that is a subject of the medical transaction;
generate the medical transaction in a second predefined format in accordance with the medical transaction to be processed by the medical claims processor by converting the extracted data into the second predefined format, wherein the second predefined format comprises at least an additional field not included in the rejected pharmacy benefit transaction;

transmit the medical transaction to the medical claims processor determined from the database;

monitor for receipt of a response associated with the medical transaction;

in an instance in which it is determined that the response to the medical transaction has not been received and a timeout occurs, generating an inclusive response including a transaction identifier and transmitting the inclusive response to the source for provision to a user; and in an instance that the response is received and a timeout does not occur, receive a response to the medical transaction, generating an eligibility response comprising an indication of patient eligibility, formatting the eligibility response to be in accordance with a third predefined format associated with a pharmacy associated with the source from which the modified pharmacy benefits transaction was received, and cause transmission of the eligibility response to the source for provision to a user.

10. The computer program product of claim 9, wherein the timeout occurs if the response has not been received for a time exceeding the timeout value, and wherein the timeout does not occur if the response is received before the time exceeding the timeout value is reached.

11. The computer program product of claim 9, wherein the modified pharmacy benefits transaction comprises a medical benefit claim indicator, wherein the medical transaction comprises a medical benefit claim, and wherein the response to the medical transaction comprises an indication whether the medical benefit claim is accepted by the request processor.

12. The computer program product of claim 9, wherein the computer-executable program code instructions further comprise program code instructions to:

in an instance in which the extracted data and the additional data are determined to not include data required for generation of the medical transaction:

generate a rejection message comprising an indication of rejection of the modified pharmacy benefits transaction prior to transmission to a request processor; and cause transmission of the rejection message to the source.

* * * * *